United States Patent
Luthra et al.

(10) Patent No.: US 6,929,818 B2
(45) Date of Patent: Aug. 16, 2005

(54) METHODS AND CLINICAL DEVICES FOR THE INHIBITION OR PREVENTION OF MAMMALIAN CELL GROWTH

(75) Inventors: Ajay K. Luthra, Middlesex (GB); Shivpal S. Sandhu, Reading (GB)

(73) Assignee: BioInteractions Ltd., Berkshire (GB)

( * ) Notice: Subject to any disclaimer, the term of this patent is extended or adjusted under 35 U.S.C. 154(b) by 0 days.

(21) Appl. No.: 10/467,950

(22) PCT Filed: Feb. 15, 2002

(86) PCT No.: PCT/GB02/00672

§ 371 (c)(1),
(2), (4) Date: Feb. 11, 2004

(87) PCT Pub. No.: WO02/064127

PCT Pub. Date: Aug. 22, 2002

(65) Prior Publication Data

US 2004/0116636 A1 Jun. 17, 2004

(30) Foreign Application Priority Data

Feb. 15, 2001 (GB) .............................. 0103668

(51) Int. Cl.$^7$ ................................ A61L 33/00
(52) U.S. Cl. ................ 427/2.24; 427/2.25; 424/423
(58) Field of Search ................. 427/2.1, 2.24; 424/405, 422, 423

(56) References Cited

U.S. PATENT DOCUMENTS

| | | | |
|---|---|---|---|
| 2,084,466 A | | 6/1937 | Ukropina |
| 3,695,921 A | | 10/1972 | Shepherd et al. |
| 4,479,795 A | | 10/1984 | Mustachich et al. |
| 4,581,028 A | | 4/1986 | Fox et al. |
| 4,678,660 A | | 7/1987 | McGary et al. |
| 4,713,402 A | | 12/1987 | Solomon |
| 4,891,423 A | | 1/1990 | Stockel |
| 5,142,010 A | | 8/1992 | Olstein |
| 5,288,503 A | * | 2/1994 | Wood et al. ............... 424/497 |
| 5,451,424 A | * | 9/1995 | Solomon et al. ........... 427/2.1 |
| 5,817,325 A | * | 10/1998 | Sawan et al. ............. 424/411 |
| 5,886,048 A | | 3/1999 | Kirschner et al. |

FOREIGN PATENT DOCUMENTS

| | | |
|---|---|---|
| EP | 0379269 | 7/1990 |
| EP | 0490250 | 6/1992 |
| GB | 2084466 A | 4/1982 |
| GB | 2349644 | 11/2000 |
| JP | 57/171913 | 10/1982 |
| JP | 59/228856 | 12/1984 |
| JP | 5097697 | 4/1993 |
| JP | 06-36064 A | 2/1994 |
| RO | 112577 | 11/1997 |
| RO | 113302 | 6/1998 |
| WO | WO 86/02561 | 5/1986 |
| WO | WO 95/04520 | 2/1995 |

OTHER PUBLICATIONS

Mariotti et al., Chlorohexidine–induced Changes to Human Gingival Fibroblast Collagen and Non–collagen Protein Production, Journal of Periodontology, vol. 70, No. 12, Dec. 1999.*

Gottsauner–Wolf et al. in Clin. Cardiol. 19, 347–356 (1996) "Restenosis—an open file".

Mariotti, et al., "Chlorhexidine–induced changes to human gingival fibroblast collagen and non–collagen protein production" Journal of Periodontology, vol. 70, No. 12, Dec. 1999.

Pitfield, et al., "Effect of chlorhexidine on gingival epithelial cell growth and migration", Journal of Dental Research, vol. 72 p. 336 (Abstract).

Shakespeare et al., "Effects of proprietary oral rinses containing chlorhexidine, hexetidine and benzydamine on the proliferation of human buccal epithelial cells in culture." Archives of Oral Biology England 1988, vol. 33, No. 12.

Xu, "In Vitro Prompt killing by chlorhexidine of human colorectal carcinoma cell lines." Chinese Jouranl of Surgery (1990) vol. 28, No. 1.

* cited by examiner

Primary Examiner—Timothy Meeks
Assistant Examiner—William Phillip Fletcher, III
(74) Attorney, Agent, or Firm—Patterson, Thuente, Skaar & Christensen, P.A.

(57) ABSTRACT

Certain embodiments of the invention set forth materials and methods for inhibiting mammalian cell growth by use of a chemical material containing at least one biguanide group, —NH—C(NH)—NH—C(NH)—NH—, in the preparation of, e.g., a medicament or medical device. The chemical material may be, e.g., monomeric or polymeric.

28 Claims, No Drawings

METHODS AND CLINICAL DEVICES FOR THE INHIBITION OR PREVENTION OF MAMMALIAN CELL GROWTH

FIELD OF THE INVENTION

This invention relates to the inhibition of cell growth, more particularly it relates to the inhibition of mammalian cell growth. In one embodiment it relates to the preparation of medical compositions for treatments for the inhibition of mammalian cell growth. In another embodiment it relates to the inhibition of mammalian cell growth where tissue growth is a problem, e.g. in the case of cancerous growths, or in the vicinity of implanted clinical devices. Still more particularly it relates to the prevention or inhibition of restenosis for articles such as stents implanted in blood vessels after angioplasty. More specifically, the invention concerns the use of monomeric or polymeric biguanides to inhibit mammalian cell growth. In one particular embodiment, it relates to the use of a family of polymeric materials incorporating biguanide compounds pendant to the polymer chain in the production of articles of manufacture in particular medical devices.

Biguanides are a family of chemical compounds that contain a grouping of the formula:

—NH—C(NH)—NH—C(NH)—NH— the terminal nitrogen atoms being attached to any of a broad range of groups, and many of them have previously been identified as having powerful antimicrobial activity. Their action on mammalian cells, however, has been far less intensively investigated.

BACKGROUND

Under normal conditions, cell growth occurs throughout the life of the organism. Usually this proceeds in the manner that is normal for the particular part of the body of that organism, but occasionally in specific instances such as healing of tissues, additional growth is needed until the tissue is repaired, at which time it should cease, and normal functioning be resumed. Occasionally, however, the normal growth-inhibiting factors cease to operate and cell growth continues unchecked.

There are several clinical areas in which mammalian cell growth poses a problem. Atherosclerosis, a major cause of death in the western world, is commonly treated by the operation of angioplasty. This produces the immediate effect of dilation of the blood vessel, but there is a continuing problem of restenosis, i.e. narrowing of the blood vessel, because of the proliferation of smooth muscle cell, and the deposition of extracellular matrix proteins such as collagen.

Similar problems resulting from undesired cell growth may be encountered after other surgical treatments, such as the installation of prostheses, implanted sensors, or implanted capsules that contain cells or release drugs.

There are, moreover, several medical conditions in which undesired growth of cells occurs, sometimes with results that are disfiguring, as in the case of the "Elephant Man", who suffered a number of highly visible growths of tissue. Previously thought to be a case of neurofibromatosis, it is now thought to be a very rare condition, known as the Proteus syndrome.

Where restenosis is concerned, because of the scale of the problem arising from the number of angioplasties now carried out with an aging population, and with the tendency among western peoples to adopt an unsatisfactory diet, there have been intensive efforts to alleviate restenosis, see the review article "Restenosis—an open file" by Gottsauner-Wolf et al. in Clin. Cardiol. 19, 347–356 (1996). A wide variety of pharmaceuticals have been studied, and some success has been achieved with platelet inhibitors, glycoprotein IIIb/IIIa receptor antagonists, and the use of intracoronary metallic stents. There is still, however, a need for effective means of alleviating the problem of stenosis.

SUMMARY AND DESCRIPTION OF PREFERRED EMBODIMENTS

It is clear, therefore, that there are many medical fields in which a simple means of inhibiting undesired cell growth is urgently needed.

Certain embodiments of the invention provide a solution to this problem.

Certain embodiments provide compositions that can be administered to a patient orally, or by injection, or by implantation.

Certain embodiments provide compositions that can be applied to surgical devices, including but not limited to stents, stent grafts, vascular grafts and surgical prostheses, to inhibit restenosis and other undesired cell growth.

Certain embodiments provide compositions that can be used to manufacture surgical devices, including but not limited to stents, stent grafts, vascular grafts and surgical prostheses, to inhibit restenosis and other undesired cell growth.

Certain embodiments provide compositions that comprise or can be used in conjunction with the biguanide that also contain anti-cancer agents, antibiotic agents and/or drugs. The purpose of these compositions is to provide an action of the biguanide that facilitates entry of the agent or drug through the cell wall. The object is to allow lower dosage of the agent or drug, thereby reducing the side effects of the agent or drug.

The agent or drug may be eluted from a medical device whereas the biguanide may be bound to or associated with especially the surface of the medical device or may also be eluted with the agent or drug. Such agents or drugs may be, but are not restricted to, rapamycin, actinomycin, and taxol.

Our prior British Patent Application GB-A-2349644, and corresponding International Patent Application PCT/GB00/0164, disclose polymeric materials incorporating a biguanide compound pendant to the polymer chain, and chemically bonded thereto through some but not all of the amine nitrogen atoms of the biguanide compound. The present Application incorporates by reference these applications.

According to one embodiment, the present invention provides a method of inhibiting undesired cell growth by bringing cells that may proliferate undesirably into effective exposure to a composition comprising at least one biguanide.

According to another embodiment, the present invention provides a method of providing a medical device with the property of inhibiting undesired cell growth, by manufacturing said device with a composition comprising at least one biguanide, adapted to bring cells that may proliferate undesirably into effective exposure to said biguanide. This may be achieved by employing a composition that will provide a permanent covalent linking of the biguanide to the device. Alternatively, the biguanide may be included in a water-insoluble composition deposited on the medical device, or a high-molecular weight composition such as a polymer biguanide, may be entrapped or adsorbed on the medical device. Another method is to complex a biguanide with a metal. In general, the biguanide, either in monomeric or polymeric form, can be applied to the medical device from an organic or aqueous system or from water. The biguanide in monomeric or polymeric form can be caused to bind to the medical device by absorption, adsorption, ionic interaction, or covalent attachment. Alternatively the biguanide need not be attached to the medical device but may be released close to the device or to the portion of the patient's anatomy that is to be protected from undesired cell growth by any conventional drug delivery means, e.g. polymer, liposomes, balloon catheters, etc.

According to another embodiment, the present invention relates to the use of a composition comprising at least one biguanide in a method of providing a medical device with the property of inhibiting undesired cell growth, in the manufacture of said device whereby, in use, said device will be capable of bringing cells that may proliferate undesirably into effective exposure to said biguanide.

According to another embodiment, the present invention relates to the use of a composition containing at least one biguanide group together with at least one additional material having a physiological or psychotropic action. Such compositions may be used either for direct administration, or may be applied to medical devices, in the same manner as the compositions described above.

Generally, this invention is directed to inhibiting, fully or partially, cellular encroachment, restenosis, and the like, by exposing cells to biguanides. One way in which this may be done in accordance with the invention is to associate the biguanide with an implant. Generally the biguanides may be bound to a surface or released. Binding to a surface may be achieved by numerous methods including, but not limited to, adsorption, mixing, covalent bonding, ionic interaction, coulombic interaction, hydrogen bonding, interpenetrating networks, or crosslinking.

The release of biguanides may be accomplished by the use of controlled release mechanisms, mechanisms that rely on a coating, multiple coatings, microspheres, liposomes, pumps, gels, mixes, coacervates, leaching, dissolving, eroding, cell-mediated erosion, etc. The biguanides are a large class of compounds, and are useful in accordance with the present invention because of their effect on cells similar to that of chlorhexidine and polyhexanide. The biguanides may be used in admixture with pharmacologically active and/or inert substances.

The biguanides used in accordance with the invention may be coated on, or directly attached to, materials used in the manufacture of medical devices, such as polymers, metals, or ceramic materials for stents, stent grafts, vascular grafts and surgical prostheses.

The biguanides used in accordance with the invention may be used in conjunction with one or more additional materials having a physiological or psychotropic action.

Fabrication of medical apparatus is usually from metals or polymeric materials that may comprise, but are not limited to, polyurethanes, silicones, polyvinylchloride and others, by moulding and extrusion techniques.

Although many attempts have been made to eradicate the problem of infection on medical apparatus, we are presently unaware of any proposals to provide such apparatus with a means of inhibiting mammalian cell growth. Documents that disclose the attachment of an infection resistant material to the polymeric apparatus include U.S. Pat. Nos. 3,695,921; 4,581,028; 4,479,795; 2,084,466; 4,713,402; 4,678,660; and 5,451,424.

A number of documents disclose the use of various biguanides for providing medical devices with antiseptic properties.

Japanese Patent Application No. 60/36064 discloses the adsorption of chlorhexidine on to the surface of polyurethane or silicone catheter by dipping into an aqueous solution of chlorhexidine which is then converted into a water insoluble form by dipping into a solution of an acid.

Japanese Patent Application No. 59/228,856 discloses an elastomeric catheter possessing a water insoluble biguanide or salt as a thin coating on the surface.

PCT Application No. WO 86/02561 discloses a thermoplastic polymer having up to 1% chlorhexidine contained in or upon the surface.

UK Patent Application No. 2084466A discloses a procedure for rendering polypropylene apparatus biocidal with chlorhexidine base, and suggests that the apparatus may be prepared from other plastics.

U.S. Pat. No. 4,891,423 discloses linear polyoxyalkylene diamine biguanides and discusses other known biguanides, and their use in solid and liquid bactericidal and fungicidal compositions, including ophthalmic saline solutions.

U.S. Pat. No. 5,142,010 discloses the vinyl copolymerisation of certain polymerisable unsymmetrical biguanide compounds.

U.S. Pat. No. 5,817,325 discloses crosslinking biguanide polymers with, inter alia, isocyanates or epoxides to form an immobile, insoluble, non-leachable surface matrix which has the ability to deliver deposited biocidal silver salts into a the interior of a micro-organism. The polymers are useful for coating contact lens cases and other articles. The biocidal action is through the silver salts, not through the highly cross-linked biguanides.

In accordance with the invention, novel chemically modified mammalian cell growth inhibiting materials are produced by the chemical modification of biguanide compounds to produce polymers that can be blended into the bulk of other polymers, be used as coatings or in deposits, or be chemically attached to the surface of, or otherwise associated with, a medical device.

A medical device in accordance with the invention may be made of, coated with, or surface treated to form in situ, the novel polymers having pendant biguanide groups.

Biguanides are strongly basic compounds containing the biguanide group: —NH—C(NH)—NH—C(NH)—NH—.

—NH—C(NH)—NH—C(NH)—NH— have previously been identified as having powerful antimicrobial activity.

Two particularly preferred biguanides for the purposes of the present invention are polyhexanide and chlorhexidine, which are commercially available. Each includes the biguanide group adjacent a hexamethylene chain. Their respective structures can be represented as follows:

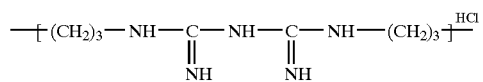

Polyhexanide hydrochloride salt

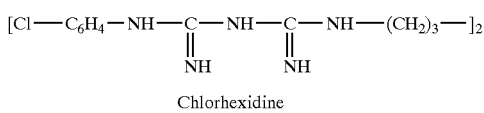

Chlorhexidine

Polyhexanide and chlorhexidine have a broad spectrum of anti-bacterial activity and at relatively low concentrations the anti-bacterial action is bacteriostatic; at higher concentration the action becomes rapidly bactericidal. The commercial water soluble salt of chlorhexidine is usually the digluconate.

In one aspect of the invention, biguanides are chemically modified to yield novel chemically modified materials that inhibit mammalian cell growth.

In another aspect of the present invention the chemically modified material is applied to medical devices to render them inhibitory of mammalian cell growth.

In accordance with a further aspect of this invention, the application of the chemically modified material to a medical device produces stable, non-leaching material that is inhibitory of mammalian cell growth.

Without wishing to be bound by any particular theory, it is believed that the mammalian cell growth inhibitory activity of biguanide compounds derives from the strongly basic character of their biguanide groups which form acid addition salts with a cationic charge delocalised over the five neighbouring secondary amine nitrogen atoms. This enables the biguanide to be rapidly attracted to a negatively charged cell. Thereafter the biguanide interacts with the cytoplasmic membrane, upsetting the ionic balances and, ultimately, disrupting the membrane and causing irreversible damage to the cell contents.

The present invention utilises the amino nitrogen atoms of the biguanide group to anchor these mammalian cell growth inhibitory compounds to a polymeric substrate as pendant species without disabling their mammalian cell growth inhibitory properties, although the normal acid addition salt form of these compounds interferes with their derivatisation at these amino sites. The polymeric products of the invention are thus distinguished from both linear polymeric biguanides and highly cross-linked biguanide polymers.

In accordance with one embodiment of the invention, there is provided a polymeric material incorporating a mammalian cell growth inhibitory biguanide compound pendant to the polymer chain, being chemically bound thereto through some but not all of the amine nitrogen atoms, and preferably of the secondary amine nitrogen atoms of the —NH—C(NH)—NH—C(NH)—NH— biguanide group or groups, of the inhibitory biguanide compound. The pendant biguanide compounds are generally bound through the secondary amine nitrogen atoms, which may include some of the >C=NH imino nitrogen atoms, and may include some of the C—NH—C secondary amine nitrogen atoms. However, a certain amount of binding through the primary amine groups at each end of biguanides such as polyhexanide is also possible.

There is also provided a medical device comprising a polymeric material incorporating a pendant mammalian cell growth inhibitory biguanide compound chemically bound to the polymer through some but not all of the amine nitrogen atoms of the biguanide, and particularly the secondary amine nitrogen atoms of the —NH—C(NH)—NH—C(NH)—NH— biguanide group or groups of the biguanide compound. Such a medical device may be formed from or coated with the polymeric material incorporating the biguanide compound, or the medical device may first be formed from or coated with polymeric material which is thereafter chemically bound to some but not all of the nitrogen atoms of the biguanide compound, or the medical device may first be formed from or coated with polymeric material which is thereafter chemically bound to the residuum of a non-polymeric compound that has been bound to some but not all of the nitrogen atoms of the biguanide compound.

In other words, the biguanide can be incorporated as a pendant group into a polymer which is then made into or coated on to an article, or the biguanide can be chemically linked to polymer already on an article, or the biguanide can be bound to polymer on an article through an intermediate non-polymeric compound. Such a compound requires one functionality to bind with the biguanide secondary amine, and one functionality to bind with the polymer.

Polymer functionality to bind with the material inhibiting mammalian cell growth directly (either to the biguanide secondary amine or to a functional group on a bound non-polymeric compound as described above) may include groups such as hydroxyl (—OH), carboxyl (—COOH), anhydride (—CO—O—CO—), isocyanate (—NCO), allyl, vinyl, acrylate, methacrylate, epoxide, sulfonic (—SO$_3^-$) or sulfate (—SO$_4^-$) groups. Linkage to the polymer may be by covalent bonding (including grafting) or by ionic bonding.

Chemical binding to a secondary amine nitrogen atom by means of isocyanate results in a substituted urea linkage, or by means of isothiocyanate results in a substituted thiourea linkage, or by means of epoxide results in a beta-hydroxyl-tertiary amine, or by means of acid chloride results in a N,N-disubstituted amide, or by means of acid anhydride results in a N,N-disubstituted amide, or by means of aldehyde or ketone results in N,N-disubstituted hemiaminals or aminals depending on the aldehyde or ketone, or by means of unsaturated bonds results in a tertiary amine linkage.

Suitable medical devices to which the invention may be applied include catheters, vascular grafts, stents, stent grafts, heart valves and pumps.

In a further aspect, the invention provides a method of making polymeric material which comprises chemically binding reactive sites on a polymeric material with some but not all of the amine nitrogen atoms of a biguanide compound, especially the secondary amine nitrogen atoms of the —NH—C(NH)—NH—C(NH)—NH— biguanide group or groups of a biguanide compound. The secondary amine nitrogen atoms bound to the reactive sites may include some of the >C=NH imino nitrogen atoms and may include some of the C—NH—C nitrogen atoms. Primary amine end groups on suitable biguanide compounds, such as polyhexanide, may also participate in binding to polymeric materials.

In an important aspect of the method, it comprises the preliminary step of forming a free base, preferably a partial free base, of the biguanide compound before binding the reactive sites with the nitrogen atoms. By removing some but not all of the acid of the usual acid addition salt, some of the secondary amine nitrogen atoms become available for derivatisation. If the entire free base is liberated, care needs to be taken to ensure only partial derivatisation.

The preferred reactive sites to bind with the biguanide nitrogen comprise isocyanate, isothiocyanate, epoxide, acid chloride, acid anhydride, aldehyde, ketone and unsaturated (especially acrylate, methacrylate and vinyl) sites.

Similar considerations apply to a variation of the above method which comprises modifying a polymer precursor by chemically binding some but not all of the amine nitrogen atoms of a biguanide compound, especially the secondary amine nitrogen atoms of the —NH—C(NH)—NH—C(NH)—NH— biguanide group or groups of a biguanide compound with reactive sites on the polymer precursor, and thereafter converting the so modified polymer precursor to a polymeric material by a method including a polymerisation step which leaves the biguanide compound residue pendant to the polymer chain.

The reactive sites on the polymer precursor may comprise isocyanate, isothiocyanate, epoxide, acid chloride, acid anhydride, aldehyde, ketone or unsaturated sites, or other suitable sites. Even sites comprising hydroxyl, carboxyl or amino groups can link on to the biguanide groups by using coupling agents such as carbonyl diimidazole or carbodiimides.

The polymer precursor may also contain acrylate, methacrylate, allyl or vinyl groups, and the polymerisation step may be carried out by polymerising the modified polymer precursor through the said groups. Any other polymerisable group may also be used.

Similar considerations apply to a further variation of the foregoing method of making polymeric material that inhibits mammalian cell growth which comprises modifying a non-polymeric compound by chemically binding some but not all of the amine nitrogen atoms of a biguanide compound, especially the secondary amine nitrogen atoms of the —NH—C(NH)—NH—C(NH)—NH— biguanide group or groups of a biguanide compound with reactive sites on the non-polymeric compound, and thereafter chemically binding the so modified compound to a polymeric material. The chemical binding of the material inhibiting mammalian cell growth to the polymeric material may be by covalent bonding (including grafting) or by ionic bonding.

The non-polymeric compound may also contain acrylate, methacrylate, allyl or vinyl groups, so that the modified compound may be chemically bound to a polymeric material through the said groups. Any other polymerisable group may also be used. Other functional groups carried by the non-polymeric compounds for binding with polymeric materials may include hydroxyl, carboxyl, amide, amino, epoxide, isocyanate, sulfate, sulfonate and others. In general, it is possible to provide functionality that can react with available complementary chemical constituents contained in polymeric materials to form polymeric mammalian cell growth inhibitory materials or to covalently attach to surfaces.

Whichever method of preparation is used, the resulting polymer containing biguanide groups may be subsequently blended with other polymeric material to form a polymer blend for use in forming an article of manufacture, and preferably blended with medically acceptable polymeric material to form a polymer blend for use in the manufacture of a medical device.

Typical materials for blending include polyurethanes, polyamides, latex, silicones, siloxanes, polyvinyl chloride, polyesters, polycarbonates, polyacrylonitrile, polymethylmethacrylate, polypropylene, polyethylene and hydrogels. Clearly the biguanide polymer and the blending polymer should be suitably compatible.

In a further application of the invention, the polymer containing biguanide groups may subsequently be coated on to an article of manufacture to form a mammalian cell growth inhibitory coating thereon.

Chlorhexidine and polyhexanide are the preferred biguanide compounds. Each has its own activity spectrum. To broaden the mammalian cell growth inhibitory range of the end product, the invention includes the further step of blending the resulting polymers containing biguanide groups derived from both chlorhexidine and polyhexanide, or copolymerising precursors to form a polymer in accordance with the invention containing biguanide groups derived from both chlorhexidine and polyhexanide.

The mammalian cell growth inhibiting material may exist in the free base or acid form or the salt thereof and as such the invention does include such forms.

To illustrate the invention by a general example, an amino constituent contained in the mammalian cell growth inhibiting material (MCGIM) is able to react with a polymeric isocyanate (P-NCO) constituent to form a urea linkage giving a polymeric infection resistant material, as outlined in Scheme 1 a), b) and c). The converse is also true where the MCGIM contains isocyanate constituents and is able to react with polymeric amino.

Scheme 1

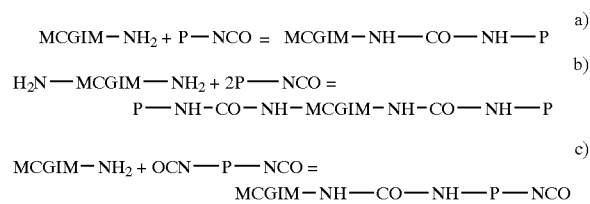

Polymeric Materials (PMCGIM) prepared as in Scheme 1 may be constituted, by way of example, into homogeneous blends of extrudable polyurethane to form medical apparatus with mammalian cell growth inhibiting properties that are effective and stable, in which the PMCGIM is unable to permeate to body tissue or fluids.

By way of another example the PMCGIM is prepared and dissolved in a suitable solvent for coating the medical article in order to give it mammalian cell growth inhibiting properties that are effective and stable, in which the PMCGIM is unable to permeate to body tissue or fluids.

By way of a further example the chemically modified MCGIM (e.g. MCGIM-NH$_2$) is attached to the surface by conventional chemical linkages. In the case of MCGIM-NH$_2$, one such method would by way of an amide bond.

An example of chemical modification, in relation to polyhexanide, is the reaction of an isocyanate to the secondary amine, as shown by Scheme 2, to give substituted ureas.

Scheme 2

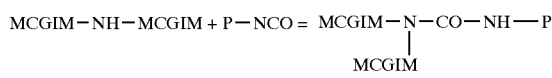

The polyisocyanates useful in the invention in producing substituted ureas with the MCGIM, typically polyhexanide, may be selected from a wide range of aliphatic, cycloaliphatic, and aromatic polyisocyanates. The isocyanate groups may be carried on polymers having unsaturated alkyl groups, esters, ethers, siloxanes, urethanes, amides, carbonates, and mixtures thereof which can be chosen to promote compatibility with other polymers that they may subsequently be coated on or blended with.

Polydiisocyanates that can be utilised are those typically used in the formation of polyurethane, which when reacted with secondary amines form the substituted ureas. Additionally, polydiisocyanates can be prepared by the reaction of a polyamine or polyol with a diisocyanate, as shown by Scheme 3.

Scheme 3

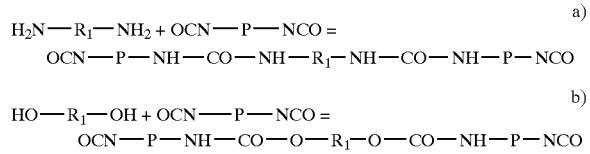

In Scheme 3, —$R_1$— and —P— can typically be aliphatic groups, cycloaliphatic groups, aromatic groups, unsaturated alkyl groups, esters, ethers, siloxanes, urethanes, amides, carbonates, and mixtures thereof. Others are of course possible.

Such polydiisocyanates may then be further reacted with MCGIM containing appropriate reactive chemical groups, an example being the secondary amine of polyhexanide reacted with the isocyanates, as shown in Scheme 4; thus producing Polymeric MCGIM (PMCGIM).

Scheme 4

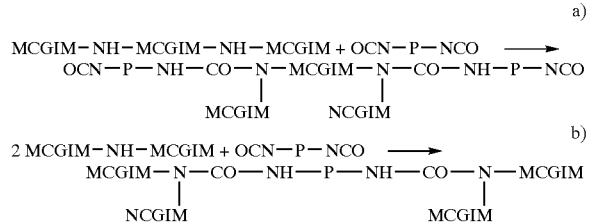

The PMCGIM can be compounded with other polymers, such as polyurethanes, polysiloxanes, polyesters, polyvinylchlorides, polybutadienes and polyamides, to produce medical apparatus, either by extrusion or moulding, that is mammalian cell growth inhibiting. The active ingredient (MCGIM) is stable within the medical apparatus and is non-leaching.

The PMCGIM or the MCGIM may contain allyl, vinyl, acrylate or methacrylate groups for polymerisation to form allyl, vinyl, acrylate, and methacrylate type polymers.

Allyl, vinyl, acrylate and methacrylate functionalities can be incorporated in the MCGIM by reacting the acid chloride, isocyanate, epoxide or anhydride of a molecule containing the above double bond functionality.

For instance, methacryloylchloride can be reacted with the secondary amine of a biguanide resulting in the formation of a tertiary amide with the liberation of hydrogen chloride which re-forms the hydrochloride on the biguanide group.

Isocyanatoethyl methacrylate, allyl isocyanate, glycidyl methacrylate and the anhydride or mixed anhydride of methacrylic acid can undergo reactions with the free base of the biguanide to yield methacrylate and allyl functionality on the biguanide group. The isocyanate would react to form a urethane urea bond, the epoxide would react to form a tertiary amine and the anhydride to form a tertiary amide.

Methacrolein can also react with the secondary amine of the biguanide. Here the reaction is between a secondary amine and an aldehyde which can yield a hemiaminal or aminal, depending on the aldehyde.

Allyl, vinyl, acrylate and methacrylate derivatives of MCGIMs can undergo homopolymerisation or copolymerisation with numerous other molecules or polymers which have a double bond under thermal or electromagnetic radiation. The allyl, vinyl, acrylate and methacrylate derivatives of MCGIMs can be grafted on to surfaces having functional groups, e.g. OH, COOH, $SO_3^-$, $SO_4^-$, $NH_2$, by using initiators such as ferric ammonium nitrate.

Conversely the free base of the biguanide can react with acrylate and methacrylate derivatives of monomers or polymers to produce PMCGIM.

The PMCGIM may be dissolved in a suitable solvent, such as alcohols, acetone or tetrahydrofuran (THF) or mixtures thereof and coated on to medical apparatus. Dipping, spraying, or any other means by which a homogenous coating may be obtained, following by any necessary drying out, can be used to place the coating of PMCGIM on to the medical apparatus. The articles to be coated may be made of plastics, metals, composites or any other material compatible with the intended coating.

The chemical materials containing at least one biguanide group may also be employed in conjunction with one or more additional materials having a physiological or psychotropic action. The biguanide facilitate the passage of the material having a physiological or psychotropic action through the cell wall, thus allowing that material to be employed in lower dosages, thereby reducing potential side effects.

Instances of the manner in which such compositions may be employed include parenteral methods, e.g. tablets, capsules, emulsions, suspensions, or solutions; by injection, e.g. by needles or through drips; or by implantation, e.g. through degradable or non-degradable polymer carriers, or through pumps, e.g. infusion, peristalsis or osmosis.

Non-limiting examples of physiologically or psychotropically-active materials include: materials used in chemotherapy, for cancer or other conditions, including adriamycin, alkeran, Ara-C, BiCNU, Busulfan, CCNU, Carboplatinum, Cisplatinum, cytoxan, Daunorubicin, DTIC, 5-FU, fludarabine, Hydrea, Idarubicin, Ifosfamide, Methotrexate, Mithranmycin, Mitomycin, mitoxantrone, nitrogen mustard, Taxol, Velban, Vincrystine, VP-16, Gemcitabine (Gemzar), Herceptin, Irinotican (camptosar, CPT-11), Leustatin, Navelbine, Rituxan, STI-571, Taxotere, Topotecan (Hycamtin), Xeloda (Capacitabine), and Paclitaxel.; materials used for the prevention of bone metastasis or the treatment of high calcium levels, such as Zometa (zoledronic acid); materials used for the treatment of low white blood cell counts, such as Peg-Filgrastim; materials used for the treatment of anaemia, such as NESP; and antibiotics, such as Amoxicillin, Ampicillin, aminoglycosides, cefaxolin, cefepime, sirolimus, actinomycin, vancomycin.

The invention is illustrated by the following non-limiting examples. Examples 1 and 2 concern the preparation of polyhexanide partial free-base, which is necessary in order to protect some of the biologically active sites while freeing others to participate in reactions, in order to prepare active infection-resistant derivatives.

Polyhexanide is a commercial anti-microbial agent manufactured by Zeneca Biocides and can be represented by the following general formula:

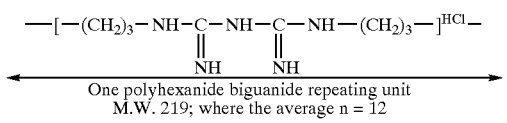

One polyhexanide biguanide repeating unit
M.W. 219; where the average n = 12

In order to derivatise polyhexanide, at least some of the hydrochloride groups must be removed. The hydrochlorides can be neutralised with a strong base, for example, sodium hydroxide.

Either all the hydrochloride groups associated with the biguanide groups of the polyhexanide can be neutralised and then the desired chemistry carried out before re-forming their hydrochloride salts or only the desired number of hydrochlorides can be neutralised and then the chemistry carried out before re-forming their hydrochlorides. Both are acceptable methods of derivatisation.

Similar considerations apply to chlorhexine and other biguanide compounds.

Various methods of producing polymers linked to biguanides are described in the following non-limiting Examples. These polymers may be employed in the production of medical devices that are resistant to mammalian cell growth, by using any of the production techniques described in our prior Applications mentioned above.

EXAMPLE 1

Polyhexanide Starting Material 400 ml of a 20% w/v aqueous solution of polyhexanide (Zeneca Biocides) was placed in a Spectra/Por® membrane (MWCO: 2,000) and was dialysed against 10 litres of deionised water for 16 hrs. The dialysed polyhexanide was then placed in stainless steel freeze-drying trays and was freeze dried for 72 hrs.

The yield of dry crystalline powder of polyhexanide was 40 g.

EXAMPLE 2

Partial Free-Base Polyhexanide

In this example only 1 in 6 biguanide hydrochloride groups are neutralised.

1 g ($4.5662 \times 10^{-3}$ moles of biguanide hydrochloride groups) of polyhexanide powder (from Example 1) was dissolved in 80 ml deionised water. The number of moles of sodium hydroxide required to neutralise 1 in 6 biguanide hydrochloride groups of polyhexanide is $7.61 \times 10^{-4}$ moles (0.0304 g, NaOH). Sodium hydroxide (0.0304 g) was dissolved in 50 ml deionised water and added drop-wise to the polyhexanide solution over a period of 1 hr. The solution was then freeze-dried yielding a dry crystalline powder of polyhexanide partial free-base (Ph.P free-base).

EXAMPLE 3

Polyhexanide/Polyisophorone Urethane Polymer 1.027 g ($7.61 \times 10^{-4}$ moles) Poly (neopentyl glycol adipate) isophorone diisocyanate terminated (PNGAID, Mn 1350) (Aldrich Chemical Co.) was dissolved in 50 ml dichloromethane. 1 g of Ph.P free-base (from Example 2) was dissolved in 50 ml ethanol and was vigorously stirred. To this polyhexanide was added the above PNGAID solution over a period of 1 hr, to form urethane urea bonds. The solution was neutralised with 0.019 ml of 4M hydrogen chloride in 1,4 dioxan.

Infrared spectrum showed the disappearance of the band at 2265.9 cm due to the N=C=O group.

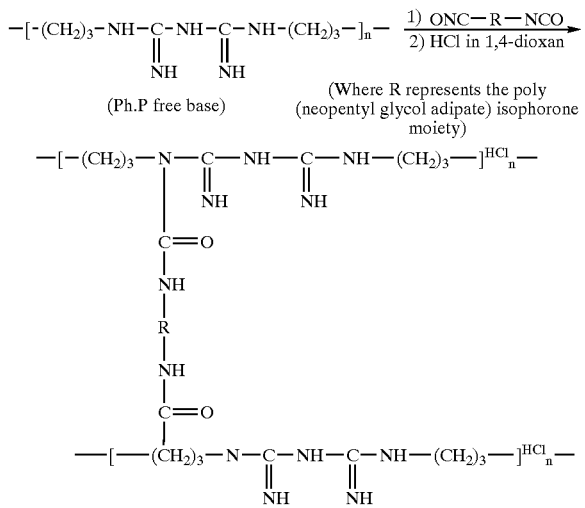

EXAMPLE 4

Polyhexanide/Silicone Copolymer 4.158 g ($3.08 \times 10^{-3}$ moles) PNGAID was dissolved in 50 ml anhydrous dichloromethane and stirred vigorously. 41.58 g ($1.54 \times 10^{-3}$ moles) aminopropyl terminated polydimethylsiloxane (APDSO with an average molecular weight of 27,000 (Gelect, Inc) was dissolved in 200 ml anhydrous dichloromethane, and was added drop-wise to the dichloromethane solution of PNGAID over a period of 2 hrs. The reaction formed urethane urea bonds between the PNGAID and APDS with the resulting copolymer terminating in isocyanate groups.

The infrared spectrum of the copolymer showed the existence of the band at 2265 $cm^{-1}$ due to the N=C=O group.

To the above PNGAID-APDS copolymer was added allylamine (0.088 g, $1.54 \times 10^{-3}$ moles) dissolved in 50 ml anhydrous dichloromethane over a period of 1 hr. This resulted in the introduction of one allyl functionality to the PNGAID-APDS copolymer leaving one reactive isocyanate.

1 g of Ph.P free-base (from Example 2) was dissolved in a mixture containing 40 ml ethanol and 10 ml dichloromethane. This solution was vigorously stirred and the above copolymer PNGAID-APDS was added dropwise over a period of 2 hrs. Infrared showed the disappearance of the N=C=O band at 2265 $cm^{-1}$. The secondary amine of the Ph.P free-base reacted with the isocyanate of the PNGAID-APDS copolymer to form a urethane urea bond.

The resulting solution was neutralised with 0.019 ml of 4M hydrogen chloride in 1,4 dioxan.

EXAMPLE 5

Extruded Silicone Sheets

The copolymer resulting from Example 4 was dried initially on a rotary evaporator and then dried under vacuum at 50° C. for 16 hrs. The yield was 47 g of polyhexanide/silicone copolymer.

The above polyhexanide/silicone copolymer (47 g) was mechanically mixed in with Silastic Q7-4736 Biomedical grade ETR (1 Kg) obtained from Dow Corning. After 1 hr of mechanical mixing, sheets were extruded and cured at 120° C. for 30 minutes.

The high consistency silicone sheets containing polyhexanide moieties had tear strengths, elongation and tensile strength equivalent to those containing no polyhexanide/silicone copolymer.

EXAMPLE 6

Polyhexanide Methacrylate 2.25 g (0.01027 moles of biguanide hydrochloride groups) of polyhexanide powder (from Example 1) was dissolved in de-ionised water. The number of moles of sodium hydroxide required to neutralise 1 in 12 biguanide hydrochloride groups of polyhexanide is $8.5616 \times 10^{-4}$ moles (0.03425 g NaOH). Sodium hydroxide (0.03425 g) was dissolved in 50 ml of de-ionised water and added dropwise to the vigorously stirred solution of polyhexanide partial free-base (Ph.P free-base).

The above Ph.P free-base was dissolved in 60 ml anhydrous dimethyl sulfoxide and stirred. 0.0895 g ($8.5616 \times 10^{-4}$ moles) methacryloyl chloride was dissolved in 25 ml dimethyl sulfoxide solution containing the Ph.P free-base over a period of 1 hr.

The above reaction involves the formation of a tertiary amide when the methacryloyl chloride reacts with the free secondary amine of the polyhexanide and the HCl liberated re-forms the hydrochloride of biguanide groups. Accordingly, when n=12, there is an introduction of one methacrylate group per polyhexanide polymer chain.

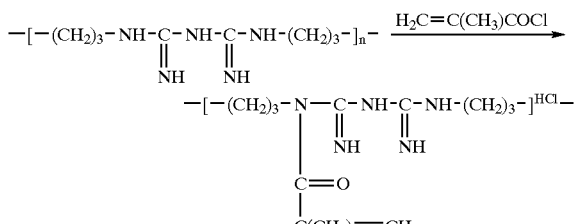

Polyhexanide methacrylate 500 ml of chloroform was then added to the above reaction mixture which precipitated the derivatised polyhexanide from solution. The solution was allowed to stand for 24 hrs at 3° C. and then washed with 3×100 ml of chloroform and then dried in a vacuum oven at 30° C. for 6 hrs.

The infrared spectrum showed the disappearance of the bands at 1765 and 1737 cm$^{-1}$ due to strong absorption of C=O unsaturated aliphatic acid chlorides.

The band due to tertiary amide

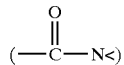

stretching in the region 1670–1630 is partially obscured by the absorption due to the polyhexanide.

EXAMPLE 7

Polyhexanide Polymer Coated Tubing 20 g of polyhexanide methacrylate was synthesised according to Example 6.

A 2 litre, 3-necked reaction vessel equipped with stirrer, thermometer, condenser and nitrogen inlet tube was charged with 1000 ml of de-ionised water and placed in a silicone oil bath at 120° C. The solution was stirred gently, and nitrogen was bubbled through the solution (40 cm$^3$/min).

40 g methoxy polyethyleneglycol 2000 methacrylate (MPEG2000MA) (Inspec) was placed in a 1 litre beaker and dissolved with stirring in 100 ml de-ionised water. Then 36 g methoxy polyethyleneglycol 350 methacrylate (MPEG350MA) (Inspec) was poured into the MPEG2000MA solution. Then 85 g of butyl methacrylate (Aldrich) was poured into the above solution with vigorous stirring.

When the temperature in the 2 litre, 3-necked reaction vessel reached 75° C. the above monomer mixture was poured into the reaction vessel and was stirred vigorously.

20 g of polyhexanide methacrylate was dissolved in 100 ml de-ionised water and was poured into the above reaction vessel containing the monomer mixture. When the temperature inside the reaction vessel reached 80° C., 1 g potassium persulphate (dissolved in 60 ml of de-ionised water) was added to the reaction vessel.

After approximately 10 mins a white viscous emulsion polymer had formed. The polymer was cooled down to room temperature in a water bath and then poured into a dialysis membrane (MWCO 3,000–4000) and dialysed against 10 litres of water for 48 hrs. After 24 hrs, the 10 litres of water was replaced with fresh de-ionised water.

The polymer was removed from the dialysis membrane and poured into freeze-drying trays and was then freeze-dried for 72 hrs.

200 g of a dry white powder of the polymer resulted.

2 g of the above polymer was dissolved in 30 ml isopropanol and when fully dissolved to a clear solution, 70 ml of tetrahydrofuran was added. Polyvinylchloride (PVC) and polyurethane (PU) tubing were coated with this polymer by dipping the tubing into the above polymer solution and then allowing it to dry for 2 hrs. When wetted with water, both the PVC and PU tubings were completely wetted out and were highly lubricious. 10 PVC and 10 PU (length 5 cm) tubings were then incubated at 37° C. in de-ionised water (100 ml) for 72 hrs. They were then removed, washed and tested for wetting. Again both sets of tubings were completely wetted out and there was no diminishing in the lubricity. The de-ionised water in which the PVC and PU tubes were incubated was freeze-dried and re-constituted in 3 ml de-ionised water and the absorbance of the solution was measured at 250 nm. No absorption was detected due to the polyhexanide. A 0.0025% w/v solution of polyhexanide, which was used as the control, had an absorption of 0.35 o.d.

EXAMPLE 8

Chlorhexidine Methacrylate 1 g ($1.9784 \times 10^{-3}$ moles) chlorhexidine (Aldrich) was dissolved in 100 ml anhydrous dichloromethane and stirred vigorously. 0.207 g ($1.9784 \times 10^{-3}$ moles) methacryloylchloride was dissolved in 50 ml anhydrous dichloromethane and added drop-wise to the chlorhexidine solution over a period of 1 hr. Methacryloylchloride reacted with the secondary amine of the chlorhexidine forming a tertiary amide. The hydrogen chloride liberated formed one hydrochloride on the chlorhexidine. The reaction was followed by infrared and observed the disappearance of the peaks of methacryloylchloride.

Chlorhexidine methacrylate monohydrochloride was formed in the above reaction. In order to obtain the dihydrochloride, 0.495 ml of 4M hydrogen chloride in 1,4 dioxan was added to the reaction mixture.

The solvent was rotary evaporated off to leave a dry powder of chlorhexidine methacrylate dihydrochloride (CMD).

EXAMPLE 9

Chlorhexidine Methacrylate 1 g ($1.9784 \times 10^{-3}$ moles) chlorhexidine was dissolved in 100 ml anhydrous dichloromethane and stirred vigorously. 0.3067 g ($1.9784 \times 10^{-3}$ moles) 2-isocyanatoethyl methacrylate (IEM) was dissolved in 50 ml anhydrous dichloromethane and added drop-wise to the chlorhexidine solution over a period of 1 hr. IEM reacted with the secondary amine of the chlorhexidine to form a urethane urea bond. Infrared showed the disappearance of the isocyanate peak due to IEM.

The above reaction resulted in the formation of chlorhexidine methacrylate. In order to obtain the dihydrochloride, 0.99 ml of 4M hydrogen chloride in 1,4 dioxan was added to the reaction mixture. The solvent was rotary evaporated to yield chlorhexidine methacrylate dihydrochloride.

EXAMPLE 10

Chlorhexidine Amide Linkage with Methacrylic Acid 1 g ($8.293 \times 10^{-3}$ moles) trimethylacetyl chloride was dissolved in 50 ml anhydrous dichloromethane. To this was solution added 0.839 g distilled triethylamine and the solution stirred. 0.714 g ($8.293 \times 10^{-3}$ moles) methacrylic acid was dissolved in 25 ml anhydrous dichloromethane and added drop-wise to the above mixture and stirred for 3 hrs at 22° C. This reaction resulted in the formation of a mixed anhydride.

$$(CH_3)_3-C-\underset{Cl}{C}=O + CH_2=C(CH_3)-\underset{OH}{C}=O \xrightarrow{triethylamine}$$

$$(CH_3)_3-C-\overset{O}{\overset{\|}{C}}-O-\overset{O}{\overset{\|}{C}}-C(CH_3)=CH_2$$

The dichloromethane was rotary evaporated leaving a liquid mixed anhydride.

1 g ($1.9784 \times 10^{-3}$ moles) chlorhexidine was dissolved in 100 ml anhydrous dichloromethane and stirred vigorously.

The above mixed anhydride was then reacted on a mole to mole basis with the chlorhexidine. The number of grams of mixed anhydride required was 0.3363 g ($1.978 \times 10^{-3}$ moles). However, to allow for the triethylamine hydrochloride in the mixture, the number of grams required is 0.61 g. Accordingly 0.61 g of the mixed anhydride mixture was dissolved in 50 ml anhydrous dichloromethane and added dropwise to the chlorhexidine solution over a period of 1 hr. The methacrylic acid formed a tertiary amide with the secondary amine of the chlorhexidine and the trimethyl acetic acid formed the counter ion to form chlorhexidine methacrylate mono trimethylacetate. 0.495 ml of 4M hydrogen chloride in 1,4 dioxan was added to form the other counter ion. The solution was rotary evaporated to dryness and a dry powder of the product obtained.

Chlorhexidine will preferentially react with the methacrylic acid of the mixed anhydride and not the trimethylacetic acid because the latter is sterically hindered.

EXAMPLE 11

Chlorhexidine Methacrylate Homopolymer 10 g (0.01978 moles) chlorhexidine was dissolved in 60 ml anhydrous dimethylsulfoxide under nitrogen at 40° C. (approximately 30 mins) in a 3-necked round bottom flask with overhead stirring. The solution was allowed to cool to room temperature and then 2.81 g glycidyl methacrylate was added, followed by 0.2 g triethylamine. The solution was allowed to react for 4 hrs at 60° C. with stirring. Then the dihydrochloride salt was formed by adding 10 ml of 4M hydrogen chloride in 1,4 dioxan to give chlorhexidine methacrylate dihydrochloride.

Nitrogen was then bubbled through the solution and the temperature of the solution allowed to reach 75° C. when 0.1 g 2,2'-azobis (2,4-dimethylvaleronitrile) was added as initiator. The solution became highly viscous after 15 min polymerisation at 80° C. and at 30 min the reaction was stopped by cooling the solution. The homopolymer of chlorhexidine was precipitated by adding 500 ml de-ionised water. The polymer was washed several times with water before drying in a vacuum oven at 60° C. for 24 hrs.

EXAMPLE 12

Chlorhexidine Methacrylate

Chlorhexidine methacrylate dihydrochloride was made exactly as according to Example 11, except that the solvent used was anhydrous chloroform. The chloroform was rotary evaporated to leave a dry white powder.

EXAMPLE 13

Chlorhexidine/Polyisophorone Urethane Polymer 3 g ($5.935 \times 10^{-3}$ moles) chlorhexidine was dissolved in 100 ml anhydrous dichloromethane with stirring. 4 g ($2.963 \times 10^{-3}$ moles) PNGAID was dissolved in 50 ml anhydrous dichloromethane and added drop-wise to the chlorhexidine solution over a period of 1 hr. When the reaction was complete, infrared showed the absence of the bond at 2265.9 $cm^{-1}$ due to N=C=O group of PNGAID. The reaction resulted in forming a urethane urea bond. 2 mole equivalent of chlorhexidine reacted with one mole equivalent of PNGAID.

Then the dihydrochloride was formed by adding 2.97 ml of 4M hydrogen chloride in 1,4 dioxan. Five 5 cm long PU tubings were dip-coated with this polymer and allowed to dry for 24 hrs. The PU tubing was then placed in de-ionised water (100 ml) at 37° C. for 72 hrs, after which the tubes were removed and the de-ionised water was freeze-dried. 3 ml of anhydrous dichloromethane was used to wash the stainless steel tray in which the de-ionised water was freeze-dried. A potassium bromide crystal was coated with the washing of dichloromethane and then infrared spectroscopy was conducted. Infrared showed no peak which related to the chlorhexidine or to the PNGAID.

What is claimed is:

1. A method of inhibiting mammalian cell growth comprising:
    associating a medical device implantable in a mammal with a material that comprises at least one biguanide group that comprises a formula of —NH—C(NH)—NH—C(NH)—NH— in a form within the material that is effective to inhibit the growth of mammalian cells, wherein the at least one biguanide group in the material inhibits growth of mammalian cells in the mammal after implantation of the medical device in the mammal.

2. The method of claim 1 wherein the material comprises a polymer, with the polymer comprising the at least one biguanide group.

3. The method of claim 2 wherein the polymer comprises more than one biguanide group per polymer.

4. The method of claim 2 wherein the number of biguanide groups per polymer is one.

5. The method of claim 1 wherein the material further comprises a member of the group consisting of an anti-cancer agent, an antibiotic, a drug, and combinations thereof.

6. The method of claim 1 wherein associating the medical device with the material comprises applying at least one layer of the material to the medical device.

7. The method of claim 1 wherein the medical device is a stent.

8. The method of claim 1 further comprising a chemical means for reacting the biguanide with the material.

9. A method comprising:
associating a medical device implantable in a mammal with a polymeric material that comprises a biguanide compound, wherein the biguanide compound is chemically bound to the polymeric material through some but not all of the amino nitrogen atoms of the biguanide compound with the biguanide compound being in a form in the material that is effective to inhibit the growth of mammalian cells, wherein mammalian cells of the mammal are exposed to the biguanide compound so that growth of the mammalian cells is inhibited.

10. The method of claim 9 wherein the biguanide compound is chemically bound to the polymer material through an at least one secondary amine nitrogen atom of the biguanide compound.

11. The method of claim 10 wherein the chemical binding to the at least one secondary amine nitrogen atom is made with a linkage selected from the group consisting of a substituted urea linkage, a substituted thiourea linkage, a N,N-disubstituted amide linkage, a N,N-disubstituted hemi-aminal linkage, a N,N-disubstituted aminal linkage, and a tertiary amine linkage.

12. The method of claim 9 further comprising a chemical means for reacting the biguanide with the polymeric material.

13. The method of claim 9 wherein the biguanide compound is a residue selected from the group consisting of chlorhexidine, polyhexidine, and combinations thereof.

14. The method of claim 9 wherein the medical device comprises the polymeric material.

15. The method of claim 9 wherein the medical device is associated with the polymeric material by coating at least a portion of the medical device with the polymeric material.

16. The method of claim 9 wherein the medical device comprises an initial material, and associating the medical device and the polymeric material comprises chemically binding some but not all of the nitrogen atoms of the biguanide compound to the initial material.

17. The method of claim 9 comprising coating the medical device with an initial material and chemically binding some but not all of the nitrogen atoms of the biguanide compound to the initial material to form the polymeric material.

18. The method of claim 9 wherein the medical device is first formed from polymeric material which is thereafter chemically bound to the residuum of a non-polymeric compound that has been bound to some but not all of the nitrogen atoms of the biguanide compound.

19. The method of claim 9 wherein the medical device is first coated with an initial material which is thereafter chemically bound to the residuum of a non-polymeric compound that has been bound to some but not all of the nitrogen atoms of the biguanide compound to thereby form the polymeric material.

20. The method of claim 9 wherein the medical device is a stent.

21. The method of claim 9 further comprising a chemical means for reacting the biguanide with the material.

22. The method of claim 9 wherein the medical device is a prosthesis, an implanted sensor, or an implanted capsule comprising cells or a drug.

23. The method of claim 9 wherein the medical device is a vascular graft.

24. The method of claim 23 further comprising implanting the vascular graft in a mammal.

25. The method of claim 9 further comprising implanting the medical device in a mammal.

26. The method of claim 9 wherein the medical device further comprises a member selected from the group consisting of an anti-cancer agent, an antibiotic agent, a drug, and combinations thereof.

27. The method of claim 9 wherein the medical device further comprises rapamycin, actinomycin, taxol, or combinations thereof.

28. The method of claim 9 wherein the medical device further comprises a medicament comprising a member selected from the group consisting of an anti-cancer agent, a drug, and combinations thereof.

* * * * *